United States Patent [19]

Kramer et al.

[11] 4,305,890

[45] Dec. 15, 1981

[54] CYCLOPROPYL DIHALO PHOSPHITES

[75] Inventors: Petrus A. Kramer; Pieter A. Verbrugge, both of Amsterdam, Netherlands

[73] Assignee: Shell Oil Company, Houston, Tex.

[21] Appl. No.: 180,776

[22] Filed: Aug. 25, 1980

Related U.S. Application Data

[62] Division of Ser. No. 133,773, Mar. 25, 1980, Pat. No. 4,285,882.

[30] Foreign Application Priority Data

Mar. 27, 1979 [GB] United Kingdom ............... 10661/79

[51] Int. Cl.$^3$ .............................................. C07F 9/206
[52] U.S. Cl. .................................... 260/941; 260/950; 260/958; 260/960
[58] Field of Search ................ 260/960, 941, 958, 950

[56] References Cited

PUBLICATIONS

Eliseenkov et al., "Chem. Abs.", vol. 64, (1966), 11074h.
Gerrard et al., "Chem. Abs.", vol. 49, (1950), 2440g.
Khairullin et al., "Chem. Abs.", vol. 64, (1966), 8062f.

*Primary Examiner*—Anton H. Sutto

[57] ABSTRACT

When the reaction of aldehydes with alkali metal trihaloacetates is carried out in the presence of a highly polar aprotic solvent (DMF, DMSO), novel organic alkali metal carbonates, which are precursors of pyrethroid insecticides, are formed in high yields and at a high rate. Novel sulfonates and dihalophosphites, derived from these carbonates have also been claimed.

6 Claims, No Drawings

CYCLOPROPYL DIHALO PHOSPHITES

This is a division, of application Ser. No. 133,773, filed Mar. 25, 1980 now U.S. Pat. No. 4,285,882.

BACKGROUND OF THE INVENTION

1. Field of the Invention

This invention relates to a process for the preparation of a compound of the general formula:

$$R^1-\underset{\underset{R^2}{|}}{\overset{\overset{CHal_3}{|}}{C}}-O-R^3 \qquad (I)$$

wherein $R^1$ represents an optionally substituted hydrocarbyl group, $R^2$ a methyl group or a hydrogen atom or $R^1$ and $R^2$, together with the carbon atom to which they are attached jointly form a cycloalkylidene group, each Hal a chlorine or bromine atom and $R^3$ (a) a group —C(O)OM, in which M represents an alkali metal atom, (b) a group —C(O)OR$^4$, in which $R^4$ represents an optionally substituted alkyl or an optionally substituted cycloalkyl group, (c) a hydrogen atom or (d) a group $R^5$ present in an acid of the general formula $R^5OH$.

2. Description of the Prior Art

Compounds of the general formula I in which $R^1$ represents a substituted cyclopropyl group, such as 2-(2,2-dimethoxyethyl)-3,3-dimethylcyclopropyl group, are intermediates in the preparation of 3-aryloxybenzyl esters of substituted 2,2-dihalovinylcyclopropanecarboxylic acids. These esters—which are also called "synthetic pyrethroids"—have exceptionally good insecticidal properties while possessing a very low mammalian toxicity (see U.S. Pat. No. 4,024,163. This combination of properties makes them of considerable interest to the agrochemical industry, and much effort has been expended in finding economical routes for their preparation.

A formyl group in an organic compound, for example, in intermediates to synthetic pyrethroids, can be converted into a $$Cl_3C-\underset{|}{CH(OH)} \text{ group}$$

by reaction with sodium trichloroacetate in the presence of 1,2-dimethoxyethane, followed by dilution of the reaction mixture with water, as described in J. Org. Chem., 32, 2166-2171 (1967). This conversion is effected by stirring the reaction mixture at room temperature for 80 hours. However, even after such a long reaction time the conversion of the starting aldehyde is far from complete. Furthermore, the compound having the group $$Cl_3C-\underset{|}{CH(OH)}$$

should be isolated from the mixture obtained after dilution with water if this compound is to be reacted with water-sensitive compounds for further conversion.

The selectivity to a certain compound, expressed in a percentage, is defined as $$\frac{a}{b} \times 100,$$

wherein "a" is the amount of the starting compound (for example, aldehyde) converted into that certain compound and "b" is the amount of converted starting compound.

The applicants have repeated this known process at a temperature of 80° C. and observed a high conversion of the starting aldehyde in less than one hour, but a low selectivity to the compounds having the group $$Cl_3C-\underset{|}{CH(OH)};$$

the selectivity to compounds formed as a result of aldol condensation being fairly high.

It has now been found that a rapid and high conversion of the starting aldehyde, the reaction time being usually between 1 and 30 minutes at ambient temperature, with a high selectivity to the compounds of formula I in which $R^3$ represents the group —C(O)OM, can be obtained by carrying out the reaction in a highly polar, aprotic, inert solvent. Moreover, the compounds of formula I in which $R^3$ represents the group —C(O)OM, being organic alkali metal carbonates, can be converted in usually high yield into, for example, compounds of formula I in which $R^3$ represents a hydrogen atom, the group —C(O)OR$^4$ mentioned sub (b) or the group $R^5$ mentioned sub (d) hereinbefore.

SUMMARY OF THE INVENTION

Accordingly, the invention provides a process for the preparation of a compound of the general formula:

$$Cl_3C-\underset{|}{CH(OH)};$$

wherein $R^1$ represents an optionally substituted hydrocarbyl group, $R^2$ a methyl group or a hydrogen atom, or $R^1$ and $R^2$, together with the carbon atom to which they are attached jointly form a cycloalkylidene group, each Hal is a chlorine or bromine atom and $R^3$ (a) a group —C(O)OM in which M represents an alkali metal atom, (b) a group —C(O)OR$^4$ in which $R^4$ represents an optionally substituted alkyl or an optionally substituted cycloalkyl group, (c) a hydrogen atom or (d) a group $R^5$ present in an acid of the general formula $R^5OH$, which process comprises reacting a carbonyl compound of the general formula:

$$R^1-\underset{\underset{R^2}{|}}{C}=O \qquad (II)$$

wherein $R^1$ and $R^2$ have the same meaning as in formula I, with a trihaloacetate of the general formula:

$$Hal_3C-\overset{\overset{O}{\|}}{C}-O-M, \qquad (III)$$

wherein Hal and M have the above-mentioned meaning, in the presence of a highly polar, aprotic, inert solvent, thus forming a compound of formula I, in which $R^3$ represents the group —C(O)OM and, if desired, converting this compound of formula I in a manner known per se into a compound of formula I, in which $R^3$ represents a hydrogen atom or the group mentioned sub (b) or (d) hereinbefore.

Many common organic solvents possess some degree of polarity arising from asymmetry in their molecules, but an essential feature of the present process is that the solvent should be "highly polar", a term used herein to denote the presence of a dielectric constant, measured at 25° C., of at least 25. The term "aprotic" as used herein denotes a solvent which is free from hydrogen atoms that are able to form hydrogen bonds with anions. These definitions are in accordance with "Physical Chemistry of Organic Solvent Systems", edited by A. K. Corrington and T. Dickinson, Plenum Press (1973), pages 332 and 333. Thus, alcohols and glycols do not come within this definition since the hydrogen atom of the hydroxyl group(s) form a hydrogen bond with the negative oxygen atom of the starting aldehyde. Benzene, carbon tetrachloride, 1,2-dimethoxyethane and pyridine also do not come within the definition since they are not highly polar. Nitromethane is highly polar and aprotic but not inert.

Suitable highly polar, aprotic, inert solvents include N,N-dimethylformamide, N,N-dimethylacetamide, dimethyl sulfoxide, hexamethylphosphorictriamide —[(CH$_3$)$_2$N]$_3$PO—, tetrahydrothiophene 1,1-dioxide (also named "sulpholane"), 3-methyltetrahydrothiophene 1,1-dioxide, N-methyl-2-pyrrolidone and acetonitrile.

Preferred carbonyl compounds of formula II are those in which $R^1$ represents an optionally substituted cyclopropyl group, particularly an optionally 3-substituted 2,2-dimethylcyclopropyl group, because such carbonyl compounds are intermediates in the preparation of synthetic pyrethroids. Among these carbonyl compounds those in which $R^1$ represents a 2-alkoxycarbonyl-3,3-dimethylcyclopropyl group, in which the alkoxy group has fewer than five carbon atoms, are preferred. This alkoxy group is preferably a methoxy or an ethoxy group; methoxy groups are most preferred. Other preferred compounds of formula II are those in which $R^1$ represents a 2-(2,2-dimethoxyethyl)-3,3-dimethylcyclopropyl group or 2-hydroxycarbonyl-3,3-dimethylcyclopropyl group.

Very good results have been obtained with compounds of formula II in which $R^1$ represents an optionally substituted alkyl group, particularly with fewer than ten carbon atoms. Examples of such alkyl groups are isopropyl, ethyl and methyl groups. Very suitable are compounds of formula II in which $R^1$ represents a cyclopropyl-substituted methyl group, particularly a 2,2-dimethyl-3-(2-oxypropyl)cyclopropylmethyl group. The carbonyl group in the acetyl group present in a 2,2-dimethyl-3-(2-oxopropyl)cyclopropylmethyl group indeed reacts accordingly to the invention, but to a very small extent only, the formyl group reacting with much higher selectivity.

Further examples of carbonyl compounds of formula II are those in which $R^1$ represents an optionally substituted cyclohexyl group, for example, an unsubstituted cyclohexyl group, or an optionally substituted aromatic group, such as an optionally substituted phenyl group, for example, an unsubstituted phenyl group.

Preferred starting compounds of formula II are: methyl 2-formyl-3,3-dimethylcyclopropanecarboxylate (compound 1),

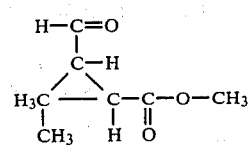

2-(2,2-dimethoxyethyl)-3,3-dimethylcyclopropanecarbaldehyde (compound 2)

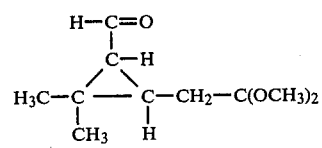

and 2,2-dimethyl-3-(2-oxopropyl)cyclopropylethanol (compound 3)

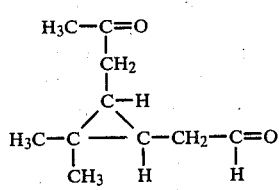

Other examples of starting compounds of formula II are n-heptanal, isobutyraldehyde, 2-butanone, acetone, cyclohexanecarbaldehyde and cyclohexanone.

Among the alkali metal atoms, M in formula III represents—i.e. lithium, sodium, potassium, rubidium and cesium—sodium and potassium atoms are preferred. Suitable starting compounds of formula III are sodium trichloroacetate and potassium trichloroacetate. If desired, the alkali metal trihaloacetate of formula III may be prepared in situ, for example, from the corresponding trihaloacetic acid and alkali metal carbonate, with simultaneous formation of the corresponding alkali metal hydrogen carbonate. Further reaction of the alkali metal hydrogen carbonate with the trihaloacetic acid should be avoided because the resulting water would impair the process of the invention. The formation of water may be avoided by using a stoichiometric excess of very finely divided alkali metal carbonate. Instead of an alkali metal carbonate an alkali metal hydride may be used, resulting in the simultaneous formation of hydrogen, or potassium fluoride, with formation of potassium hydrogen trihaloacetate fluoride.

The process of the invention is suitably carried out at a temperature between the melting point of the highly polar aprotic solvent and 60° C. Temperatures above 60° C., for example, up to 100° C., are not precluded; however, at these high temperatures the reaction time should be kept very short—for example, between 0.5 and 2 minutes to prevent decomposition of the carbonate into the corresponding alkali metal alcoholate and carbon dioxide. Very suitable temperatures are usually in the range of from 0° to 50° C. A feature of the invention is that ambient temperatures, for example, in the range of from 15° to 35° C., are most suitable.

As the alkali metal carbonate of formula I becomes available in a dissolved and/or suspended form in the highly polar aprotic inert solvent, it may be reacted in this solution and/or suspension with water-sensitive compounds, in the absence of water, for conversion into other compounds. Hence, it is not necessary to isolate the alkali metal carbonate of formula I from the reaction mixture. Four attractive examples of such conversions into other compounds are given below under (1), (2), (3) and (4).

1 The compound of formula I in which $R^3$ represents the group —C(O)OM is reacted with an alkylating or a cycloalkylating agent to give a compound of formula I in which $R^3$ represents the group —C(O)OR$^4$, with $R^4$ being an optionally substituted alkyl or an optionally substituted cycloalkyl group. The alkylating and cycloalkylating agents may be dialkyl sulfates and dicycloalkyl sulfates. The alkyl groups in the dialkyl sulfate preferably have fewer than five carbon atoms and are preferably methyl groups. For example, alkylation of sodium 2,2,2-trichloro-1-(2,2-dimethyl-3-methoxycarbonylcyclopropyl)ethyl carbonate (compound 4)

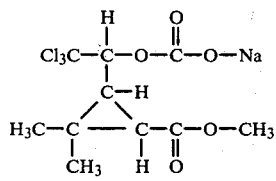

with dimethyl sulfate affords methyl 2,2,2-trichloro-1-(2,2-dimethyl-3-methoxycarbonylcyclopropyl)ethyl carbonate.

2. The compound of formula I in which $R^3$ represents the group —C(O)OM is reacted with a hydrocarbylsulfonylating agent to give a compound of the general formula I, in which $R^3$ represents a group

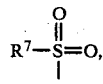

in which $R^7$ represents an optionally substituted hydrocarbyl group. The hydrocarbyl group in the hydrocarbylsulfonylating agent may be, for example, an alkyl or a cycloalkyl group. Preferred alkyl groups are those with fewer than ten carbon atoms. Very good results have been obtained with methyl groups, particularly mesyl chloride. Tosyl chloride is another example of a hydrocarbylsulfonylating agent.

3. The compound of formula I in which $R^3$ represents the group —C(O)OM is reacted with an acyl halide of the general formula $R^6$—C(O)X, or an anhydride of the general formula $R^6$—C(O)—O—C(O)—$R^6$ wherein the group $R^6$—C(O)— has the same meaning as $R^5$ in (d) mentioned above, $R^6$ represents an organic group and X a halogen atom, to give a compound of formula I in which $R^3$ represents the group $R^6$—C(O). $R^6$ suitably represents an alkyl group, particularly one with fewer than ten carbon atoms. Methyl groups are preferred. X suitably represents a chlorine or bromine atom.

4. The compound of formula I in which $R^3$ represents the group —C(O)OM is reacted with a phosphorus trihalide to give a compound of formula I, in which $R^3$ represents the group —PX$_2$, X representing a halogen atom. Chlorine and bromine are suitable halogen atoms.

According to another suitable embodiment of the invention, the compound of formula I in which $R^3$ represents the group —C(O)OM is reacted with water to give a compound of formula I in which $R^3$ represents a hydrogen atom; simultaneously, an alkali metal hydrogen carbonate is formed. The water may contain an acid, for example, hydrochloric acid or sulfuric acid, but this is not necessary.

Compounds of the general formula:

wherein $R^1$ represents an optionally substituted hydrocarbyl group, $R^2$ a methyl group or a hydrogen atom, or $R^1$ and $R^2$, together with the carbon atom to which they are attached jointly form a cycloalkylidene group, each Hal a chlorine or bromine atom and $R^3$ (i) a group —C(O)OM, in which M represents an alkali metal atom, (ii) a group —C(O)OR$^4$, in which $R^4$ represents an optionally substituted alkyl or an optionally substituted cycloalkyl group, (iii) a group

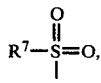

in which $R^7$ represents an optionally substituted hydrocarbyl group, or (iv) a group —PX$_2$, in which X represents a halogen atom, are believed to be novel (with the exception of 1,1,1-trichloro-2-methyl-2-propyl dichlorophosphite, 1,1,1-trichloro-2-propyl dichlorophosphite and 1-trichloromethylcyclohexyl dichlorophosphite), and the invention therefore also provides these novel compounds per se. Preferred compounds of formula I are those in which $R^1$ represents an optionally substituted cyclopropyl group, particularly an optionally 3-substituted 2,2-dimethylcyclopropyl group. Particularly preferred compounds of Formula I are those in which $R^1$ represents a 2-alkoxycarbonyl-3,3-dimethylcyclopropyl group, in which the alkoxy group has fewer than five carbon atoms and is particularly a methyl group. Other preferred compounds of formula I are those in which $R^1$ represents a 2-(2,2-dimethoxyethyl)-3,3-dimethyl-cyclopropyl group. Very suitable compounds of formula I are those in which $R^1$ represents an optionally substituted alkyl group, particularly an optionally substituted alkyl group with fewer than ten carbon atoms. Among the latter compounds those in which $R^1$ represents a cyclopropyl-substituted methyl group are preferred, particularly those having a [2,2-dimethyl-3-(2-oxopropyl)cyclopropyl]methyl group. Other examples of compounds of formula I are those in which $R^1$ represents an optionally-substituted cyclohexyl group.

Preferred compounds of formula I are: sodium 2,2,2-trichloro-1-(2,2-dimethyl-3-methoxycarbonylcyclopropyl)ethyl carbonate (compound 4), sodium 2,2,2-trichloro-1-(2-carboxy-3,3-dimethylcyclopropyl)ethyl carbonate (compound 5),

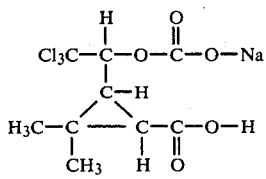

sodium 2,2,2-trichloro-1-[2-(2,2-dimethoxyethyl)-3,3-dimethylcyclopropyl]ethyl carbonate (compound 6),

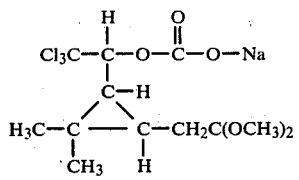

and sodium 3-[2,2-dimethyl-3-(2-oxopropyl)cyclopropyl]-1,1,1-trichloro-2-propyl carbonate (compound 7),

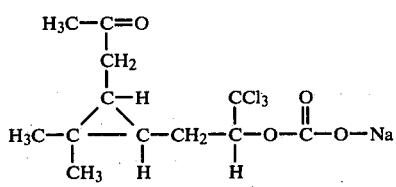

Other examples of the carbonates of formula I are: sodium 2,2,2-trichloroethyl-1-cyclohexylethyl carbonate (compound 8),

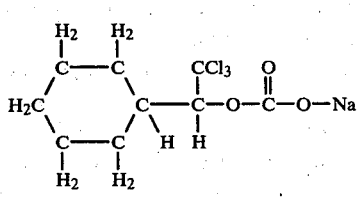

sodium 1,1,1-trichloro-3-methyl-2-butyl carbonate (compound 9),

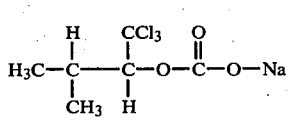

potassium 1,1,1-trichloro-3-methyl-2-butyl carbonate (compound 10),

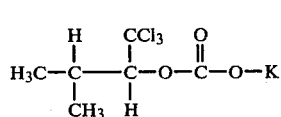

sodium 1,1,1-tribromo-3-methyl-2-butyl carbonate (compound 11),

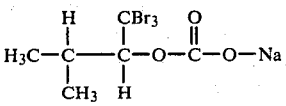

methyl 1,1,1-trichloro-3-methyl-2-butyl carbonate (compound 12),

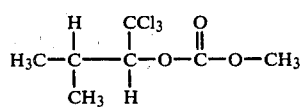

potassium 1,1,1-trichloro-2-octyl carbonate (compound 13),

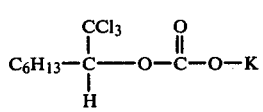

sodium 1-trichloromethylcyclohexyl carbonate (compound 14),

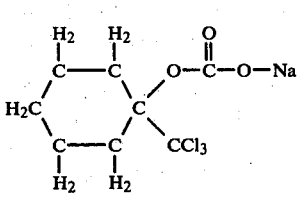

sodium 1,1,1-trichloro-2-methyl-2-butyl carbonate (compound 15),

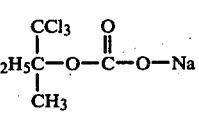

sodium 1,1,1-trichloro-2-methyl-2-propyl carbonate (compound 16)

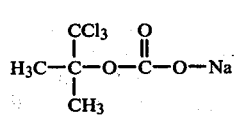

$R^7$ in the group

preferably represents an alkyl group, particularly one with fewer than 10 carbon atoms; methyl groups are most preferred. Examples of such compounds of formula I are methyl 1,1,1-trichloro-3-methyl-2-butyl sulfonate and methyl 1,1,1-tribromo-3-methyl-2-butyl sulfonate (compound 17)

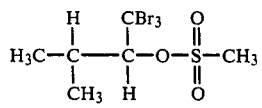  (17)

X in the group —PX$_2$ preferably represents a chlorine or bromine atom. Examples of such compounds of formula I are: 1,1,1-tribromo-3-methyl-2-butyl dichlorophosphite (compound 18),

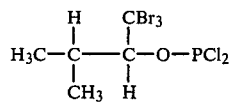  (18)

1,1,1-trichloro-2-octyl dichlorophosphite (compound 19),

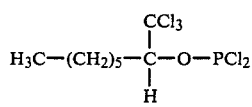  (19)

1,1,1-trichloro-2-octyl dibromophosphite (compound 20),

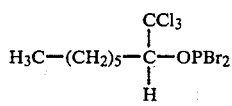  (20)

2,2,2-trichloro-1-(2,2-dimethyl-3-methoxycarbonylcyclopropyl)ethyl dichlorophosphite (compound 21),

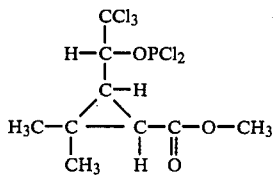  (21)

The compounds of formula I in which R$^3$ represents one of the groups —C(O)OR$^4$, R$^7$—S=O(=O)— and —PX$_2$ can be reduced with zinc and acetic acid to obtain a high yield of compounds containing a dihalovinyl group, as described in British patent application No. 79/10662, filed Mar. 27, 1979, and concurrently filed U.S. application Ser. No. 134,022.

The compounds of formula I in which R$^3$ represents the group R$^6$—C(O)— can be reduced with zinc and acetic acid to obtain a moderate yield of compounds containing a dihalovinyl group, as described in Collection Czech. Chem. Comm., 24, 2230–2236 (1959).

The dihalovinyl compounds described above wherein R$^1$ is a substituted cyclopropyl group, such as 2-(2,2-dimethoxyethyl)-3,3-dimethylcyclopropyl group, are converted to 3-aryloxybenzyl esters of substituted 2,2-dihalovinylcyclopropanecarboxylic acids, for example, as described in U.S. Pat. No. 4,222,964 and allowed U.S. Ser. No. 55,858 by hydrolyzing the dihalovinylcyclopropylethanal dimethyl acetal to the corresponding free ethanal compound followed by treatment with an alkanoic acid anhydride, e.g. in the presence of an amine, to yield a dihalovinylcyclopropylvinyl alkanoate, which when ozonized followed by oxidative decomposition, yields the free dihalovinylcyclopropanecarboxylic acid for esterification.

The invention further provides the novel compounds 2-[2,2-dimethyl-3-(2,2,2-trichloro-1-hydroxyethyl)cyclopropyl]acetaldehyde dimethyl acetal (compound 22) and

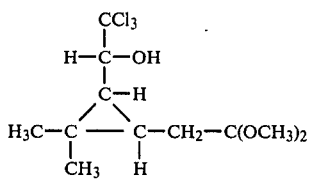  (22)

methyl 2,2-dimethyl-3-(3,3,3-trichloro-2-hydroxypropyl)cyclopropylmethyl ketone (compound 23).

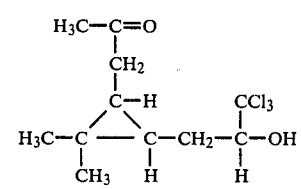  (23)

Compounds 22 and 23 may be prepared by reacting compounds 6 and 7, respectively, with water.

EXAMPLES

The following examples further illustrate the invention. Unless otherwise stated, the experiments described below were carried out at 20° C. in a three-necked flask provided with a magnetic stirrer, dropping funnel, gas meter and thermometer. The solvents were dried, for example, the N,N-dimethylformamide and dimethyl sulfoxide over molecular sieves 4 A and the 1,2-dimethoxyethane by distillation over metallic potassium.

Yields and purities were determined by nuclear magnetic resonance (NMR) spectroscopy and gas-liquid chromatography. The NMR data quoted were recorded at 90 MHz; the absorptions given are relative to a tetramethylsilane standard.

EXAMPLES I–VI

Preparation of 1,1,1-trichloro-2-octanol in six solvents

The contents of a flask charged with n-heptanal (2.5 mmol), sodium trichloroacetate (2.7 mmol) and a solvent (10 g) were stirred for 16 hours. At the end of this period, when the reaction mixture contained sodium 1,1,1-trichloro-2-octyl carbonate (compound 24),

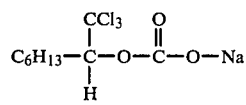  (24)

water (50 ml) was added and the mixture was extracted with two portions (each of 25 ml) of n-pentane. Six experiments were thus carried out, each with another solvent. Table I shows which solvents and temperatures were used and presents the conversion of the n-heptanal and the selectivity to the title alcohol. These conversions and selectivities were already obtained after one hour stirring, stirring being continued overnight.

TABLE I

| Example | Solvent | Dielectric Constant | Temp., °C. | Conversion of n-Heptanal, % | Selectivity to Title Alcohol, % |
|---|---|---|---|---|---|
| I | hexamethylphosphorictriamide | 29.6/25° C. | 20 | 100 | 96 |
| II | N-methyl-2-pyrrolidone | 32.2/25° C. | 20 | 100 | >90 |
| III | dimethyl sulfoxide | 46.6/25° C. | 20 | 100 | >90 |
| IV | tetrahydrothiophene 1,1-dioxide | 44/30° C. | 27 | 93 | 96 |
| V | N,N-dimethylacetamide | 37.8/25° C. | 20 | 85 | 89 |
| VI | acetonitrile[1] | 36.2/25° C. | 20 | 57 | 86 |
| Comparative Experiments: | | | | | |
| A | 1,2-dimethoxyethane | 17.2/25° C. | 20 | 4.5 | >90 |
| B | tetrahydrofuran | 7.8/15° C. & 7.2/30° C. | 20 | 0 | 0 |
| C | tetrahydrofuran | 7.8/15° C. & 7.2/30° C. | 60 | 99 | 30 |
| D | pyridine | 12.3/25° C. | 20 | 33 | 39 |
| E | nitromethane[1] | 35.9/30° C. | 20 | 100 | 0 |
| F | 1,4-dioxane | 2.2/25° C. | 20 | 0 | 0 |

[1]The sodium trichloroacetate was not completely soluble.

Comparative Experiments A-F—Preparation of 1,1,1-trichloro-2-octanol in five solvents Six experiments were carried out as described in Examples I-VI. Table I shows which solvents and temperatures were used and gives the conversion of n-heptanal and the selectivity to the title alcohol.

Comparison of Examples I-VI with the six comparative experiments shows that highly polar, aprotic inert solvents give much better results than aprotic inert solvents that are not highly polar. Nitromethane is highly polar and aprotic but not inert.

EXAMPLE VII

Preparation of 1,1,1-trichloro-2-octanol in N,N-dimethylformamide

An NMR tube was charged with n-heptanal (0.69 mmol), potassium trichloroacetate (0.69 mmol) and N,N-dimethylformamide (0.4 ml, dielectric constant 37.7 at 25° C.). After standing for 35 minutes, when the reaction mixture contained potassium 1,1,1-trichloro-2-octyl carbonate (compound 13), 36%w aqueous hydrochloric acid (0.08 ml) was added, which caused evolution of carbon dioxide. The mixture obtained was diluted with deuterochloroform (0.4 ml) and the diluted solution was washed with three portions of water (each of 0.5 ml). The conversion of n-heptanal was 87%, with a selectivity to the title alcohol of 95%.

EXAMPLE VIII

Preparation of sodium 1,1,1-trichloro-3-methyl-2-butyl carbonate (compound 9) in dimethyl sulfoxide An NMR tube was charged with isobutyraldehyde (0.49 mmol), sodium trichloroacetate (0.54 mmol) and dimethyl sulfoxide (0.4 ml). After stirring for 15 minutes at 20° C. a clear solution was obtained; more than 90% of the isobutyraldehyde was converted, with a selectivity to the title carbonate of more than 90%.

The NMR spectrum of the title carbonate showed the following absorptions:
 (a) in dimethyl sulphoxide:
 $\delta = 0.93$ ppm. doublet, $CH_3$—C—$CH_3$; $\delta = 0.97$ ppm.
 $\delta = 0.97$ ppm, doublet, $CH_3$—C—$CH_3$; $J = 7.5$ Hz
 $\delta = 2.20$ ppm, multiplet, $H$—C—$CH_3$
 $\delta = 4.90$ ppm, doublet, $H$—C—$CCl_3$; $J = 8$ Hz
 (b) in N,N-dimethylformamide:
 $\delta = 1.05$ ppm, doublet, $CH_3$—C—$CH_3$
 $\delta = 1.12$ ppm, doublet, $CH_3$—C—$CH_3$; $J = 7.5$ Hz
 $\delta = 2.30$ ppm, multiplet, $H$—C—$CH_3$
 $\delta = 5.10$ ppm, doublet, $H$—C—$CCl_3$; $J = 3$ Hz

EXAMPLE IX

Isolation of sodium 1,1,1-trichloro-3-methyl-2-butyl carbonate (compound 9)

A 10 ml flask was charged with isobutyraldehyde (4.46 mmol), sodium trichloroacetate (4.9 mmol) and N,N-dimethylformamide (2 ml). After 2 minutes' mixing and standing for one hour the flask contained a thick slurry, which was poured out into water-free diethyl ether (100 ml). After decanting the solution the solid material was separated by centrifugation and the separated solid material was dried for 1 hour at 40° C. and 80 Pa. The dried material consisted of the title carbonate and showed the following infrared absorptions (2.5 mg carbonate in 300 mg potassium bromide): medium 2880 $cm^{-1}$; very strong 1715 $cm^{-1}$, very strong 1465 $cm^{-1}$; strong 1310 $cm^{-1}$; strong 1080 $cm^{-1}$, medium 970 $cm^{-1}$; strong 840 $cm^{-1}$ and strong 780 $cm^{-1}$.

EXAMPLE X

Preparation of compound 9 and conversion thereof with acid into 1,1,1-trichloro-3-methyl-2-butanol A 100 ml flask was charged with isobutyraldehyde (44.6 mmol), sodium trichloroacetate (49 mmol) and N,N-dimethylformamide (20 ml). After fifteen minutes' stirring the flask contained a thick slurry, a precipitate of compound 9 being present. Fifteen minutes later—when 3.5 mmol of carbon dioxide had been evolved—36%w aqueous hydrochloric acid (4.3 ml) was added, resulting in further evolution of carbon dioxide (41.5 mmol in all) and in the precipitation of sodium chloride.

The mixture obtained was diluted with water (175 ml) and extracted with two portions (each of 25 ml) of n-pentane. The combined extract phases were washed with four portions of water (each of 20 ml) and the washed liquid was dried over anhydrous magnesium sulphate. The n-pentane was evaporated from the dried liquid at sub-atmospheric pressure and the residue obtained (7.0 g) was distilled at sub-atmospheric pressure giving a distillate of the title alcohol (purity 97%). The conversion of isobutyaldehyde was more than 90% and the selectivity to the title alcohol was 75%.

EXAMPLE XI

Preparation of compound 9 and conversion thereof with water into 1,1,1-trichloro-3-methyl-2-butanol A 100-ml flask was charged with isobutyraldehyde (44.6 mmol), sodium trichloroacetate (49 mmol) and N,N-dimethylformamide (20 ml). After fifteen minutes' stirring the flask contained a thick slurry, a precipitate of compound 9 being present. Fifteen minutes later—when 3.5 mmol of carbon dioxide had been evolved—water (50 ml) was added at 20° C., resulting in further evolution of carbon dioxide (8.1 mmol in all). After further additon of water (125 ml), the title alcohol was isolated as described in Example X. The conversion of isobutyraldehyde was 90%, the selectivity to the title alcohol 77% and the purity of the distillate 94%. This result is about equal to that of Example X. The combined four portions of washing water (80 ml) were acidified with 36%w aqueous hydrochloric acid (4.3 ml), which caused evolution of carbon dioxide; the acidified aqueous solution was extracted with two portions of 25 ml n-pentane, the combined extract phases were dried over anhydrous magnesium sulphate and the n-pentane was evaporated from the dried solution to give a residue (0.15 g) in which the content of the title alcohol was 95%, its yield being 2%. Hence, the total yield of the title alcohol is 79%.

COMPARATIVE EXPERIMENT G

Preparation of compound 9 in 1,2-dimethoxyethane and conversion thereof into 1,1,1-3-methyl-2-butanol A 100-ml flask was charged with isobutyraldehyde (44.6 mmol), sodium trichloroacetate (49 mmol) and 1,2-dimethoxyethane (20 ml). After 30 minutes' stirring at 80° C. the contents of the flask consisted of a thick slurry, a precipitate of compound 9 being present. A total of 5 mmol of carbon dioxide had been evolved. Then, 36%w aqueous hydrochloric acid (4.3 ml) was added which caused more evolution of carbon dioxide (18.5 mmol in all) and the precipitation of sodium chloride. The title alcohol was isolated as described in Example XI. The conversion of isobutyraldehyde was 86% and the selectivity to the title alcohol 29%. This selectivity is considerably lower than that obtained in Example X.

The experiment was repeated until a total of 5 mmol of carbon dioxide had been evolved. Then, dimethyl sulphate (50 mmol) was added and stirring was continued during 16 hours at 20° C. The reaction mixture contained 3-(1,3-dioxa-2-oxobutyl)-2,2,4-trimethylpentanal (compound 25). This

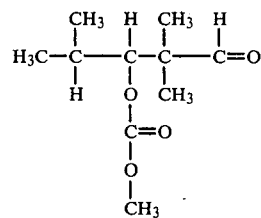

compound is believed to be novel. The NMR spectrum of compound 25 showed the following absorptions in deuterochloroform:

$\delta = 0.92$ ppm, doublet, —O—CH—CH(C$\underline{H}_3$)$_2$, J=7 Hz $\delta = 1.11$ ppm, singlet, C$\underline{H}_3$—C(CH$_3$)—C(O)H;

$\delta = 1.13$ ppm, singlet, CH$_3$—C(C$\underline{H}_3$)—C(O)H $\delta = 2.00$ ppm, multiplet, C$\underline{H}$(CH$_3$)$_2$;

$\delta = 3.83$ ppm, singlet, C$\underline{H}_3$O—

$\delta = 4.80$ ppm, doublet, $\underline{H}$C—O—C(O), J=5.5 Hz;

$\delta = 9.66$ ppm, singlet, —C$\underline{H}$(=O)

EXAMPLE XII

Preparation of compound 9 using Na$_2$CO$_3$ and conversion thereof into 1,1,1-trichloro-3-methyl-2-butanol An NMR tube was charged with trichloroacetic acid (0.91 mmol) and anhydrous sodium carbonate (1.46 mmol) and then with N,N-dimethylformamide (0.4 ml) and isobutyraldehyde (0.83 mmol). After 2 hours' shaking the tube contained a thick slurry, a precipitate of compound 9 being present. Then, 36%w aqueous hydrochloric acid (1 ml) was added and the mixture obtained was extracted with deuterochloroform (0.4 ml). The extract phase was washed with three 1-ml portions of water and then analysed. The conversion of isobutyraldehyde was 88% with a selectivity to the title alcohol of 75%.

EXAMPLE XIII

Preparation of compound 10 using K$_2$CO$_3$ and conversion thereof into 1,1,1-trichloro-3-methyl-2-butanol An NMR tube was charged with trichloroacetic acid (0.78 mmol) and anhydrous potassium carbonate (2.34 mmol) and then with N,N-dimethylformamide (0.4 ml) and isobutyraldehyde (0.70 mmol). After 2 hours' shaking the tube contained a thick slurry, a precipitate of potassium 1,1,1-trichloro-3-methyl-2-butyl carbonate (compound 10) being present. Then, 36%w aqueous hydrochloric acid (1 ml) was added and the mixture obtained was extracted with deuterochloroform (0.4 ml). The extract phase was washed with three 1-ml portions of water and then analysed. The conversion of isobutyraldehyde was 81% with a selectivity to the title alcohol of 75%.

EXAMPLE XIV

Preparation of 1,1,1-trichloro-3-methyl-2-butanol using KF

An NMR tube was charged with trichloroacetic acid (0.82 mmol) and potassium fluoride (1.0 mmol) and then with N,N-dimethylformamide (0.4 ml) and isobutyraldehyde (0.75 mmol). After 1.75 hours' shaking the tube contained a thick slurry, a precipitate of compound 10 being present. Then, 36%w aqueous hydrochloric acid (0.1 ml) was added and the mixture obtained was extracted with deuterochloroform (0.4 ml). The extract phase was washed with three 1-ml portions of water and then analysed. The conversion of isobutyraldehyde was 76% with a selectivity to the title alcohol of 75%.

EXAMPLE XV

Preparation of compound 9 using NaH and conversion thereof into 1,1,1-trichloro-3-methyl-2-butanol A 100-ml flask was charged with trichloroacetic acid (0.1 mol) and N,N,-dimethylformamide (50 ml) and then with sodium hydride (0.1 mol), thus forming sodium trichloroacetate and hydrogen. Then, isobutyraldehyde (0.1 mol) was added and the contents of the flask were stirred for 30 min. At the end of this period the temperature had risen from 20° to 35° C. The solid material present in the flask was filtered off and diethyl ether (100 ml) was added to the filtrate. After standing for 24 hours the precipitate formed was filtered off, giving compound 9 in a yield of 20%. The filtrate was washed with water, the washed filtrate was dried over anhydrous magnesium sulphate and the diethyl ether was evaporated from the dried liquid to give a residue of the title alcohol, yield 74%, the total yield of compound 9 and the title alcohol being 94%.

EXAMPLE XVI

Preparation of sodium 1,1,1-tribromo-3-methyl-2-butyl carbonate (compound 11)

Isobutyraldehyde (0.43 mmol) was added to an NMR tube charged with a solution of sodium tribromoacetate (0.47 mmol) in N,N-dimethylformamide (0.4 ml). After 5 minutes' shaking 90% of the isobutyraldehyde had been converted, with a selectivity to the title compound of 48%. The NMR spectrum of this carbonate showed the following absorptions in N,N-dimethylformamide:

δ=1.10 ppm, doublet, C$\underline{H}_3$—C—CH$_3$
δ=1.19 ppm, doublet, CH$_3$—C—C$\underline{H}_3$. J=7.5 Hz
δ=5.06 ppm, doublet, C$\underline{H}$—CBr$_3$. J=2.5 Hz

EXAMPLE XVII

Conversion of compound 11 into 1,1,1-tribromo-3-methyl-2-butanol

To the reaction mixture obtained in Example XVI—which already contained title alcohol—36%w aqueous hydrochloric acid (0.1 ml) was added and stirring was continued for 15 minutes. Then, the reaction mixture was extracted with deuterochloroform (0.4 ml) and the extract phase was washed with three portions of 1 ml water. The conversion of isobutyraldehyde was 92% and the selectivity to the title alcohol 72%.

EXAMPLE XVIII

Preparation of compound 9 and conversion thereof into methyl 1,1,1-trichloro-3-methyl-2-butyl carbonate (compound 12)

An NMR tube was charged with a solution of sodium trichloroacetate (1.1 mmol) in N,N-dimethylformamide (0.8 ml) and then with isobutyraldehyde (0.95 mmol). After 30 minutes' shaking the tube contained a thick slurry, a precipitate of compound 9 being present, and 90% of the isobutyraldehyde had been converted, with a selectivity to compound 9 of 75%. Then, dimethyl sulphate (0.95 mmol) was added and shaking was continued for 16 hours. Subsequently, 36%w aqueous hydrochloric acid (0.3 ml) was added and the mixture obtained was poured out into water (50 ml). The mixture thus formed was extracted with n-pentane (50 ml), the extract phase was washed with three 15-ml portions of water and with a saturated aqueous solution of sodium hydrogen carbonate (10 ml), the washed liquid was dried over anhydrous magnesium sulphate and the n-pentane was evaporated at sub-atmospheric pressure from the dried liquid to leave an oily residue (0.12 g) having a content of compound 12 of 88%, the yield thereof being 50%.

The NMR spectrum of compound 12 showed the following absorptions in deuterochloroform:

δ=1.09 ppm, doublet, $\underline{H}_3$C—C—CH$_3$
δ=1.16 ppm, doublet, H$_3$C—C—C$\underline{H}_3$; J=7.5 Hz
δ=2.55 ppm, multiplet, H$_3$C—C$\underline{H}$—CH$_3$
δ=3.91 ppm, singlet, C$\underline{H}_3$—O
δ=5.15 ppm, doublet, O—C$\underline{H}$; J=3 Hz.

EXAMPLE XIX

Preparation of methyl 1,1,1-trichloro-3-methyl-2-butyl sulphonate compound 26)

Isobutyraldehyde (50 mmol) was added to a solution of sodium trichloroacetate (55 mmol) in N,N-dimethylformamide (25 ml) present in a 50 ml flask. Five minutes after the addition the temperature has risen from 20° to 48° C. After 20 minutes' stirring the flask contained a thick slurry, at a temperature of 35° C. a precipitate of compound 9 being present. Ten minutes later mesyl chloride (CH$_3$SO$_2$Cl, 55 mmol) was added over a period of one hour at 20° C., which caused evolution of carbon dioxide (40 mmol). The reaction mixture was poured out into water (100 ml), which caused further evolution of carbon dioxide; the mixture obtained was allowed to separate into an aqueous and an organic layer, the organic layer was washed with three portions of 15 ml water, the washed organic liquid was dried over anhydrous magnesium sulphate and the solvent was evaporated from the dried liquid at sub-atmospheric pressure to give a yellow oil (10.46 g). The conversion of isobutyraldehyde was more than 95%, with a selectivity to the title sulphonate of 32%. The yellow oil contained 1,1,1-trichloro-3-methyl-2-butanol in a yield of 40%.

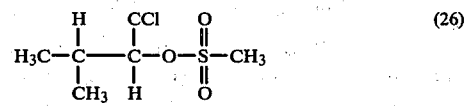

The oil was dissolved in n-pentane (100 ml), the solution was cooled to −70° C. and the precipitate formed was filtered off and dried to give yellow brown crystals (3.6 g) having a content of the title sulphonate of 91%.

The NMR spectrum of the title sulphonate showed the following absorption in deuterochlorofrom:

δ=1.16 ppm, doublet, $\underline{H}_3$C—C—CH$_3$
δ=1.22 ppm, doublet, H$_3$C—C—C$\underline{H}_3$; J=7.5 Hz
δ=2.62 ppm, multiplet, H$_3$C—C$\underline{H}$—CH$_3$
δ=3.28 ppm, singlet, SO$_2$C$\underline{H}_3$
δ=4.99 ppm, doublet, Cl$_3$C—C$\underline{H}$

EXAMPLE XX

Preparation of 1,1,1-trichloro-2-octyl dichlorophosphite (compound 19)

A 10-ml flask was charged with potassium 1,1,1-trichloro-2-octyl carbonate (compound 13, 0.86 mmol)

and phosphorus trichloride (1.0 mmol) and stirred at 40° C. for 1.25 hours. Then, the excess of phosphorus trichloride was evaporated at sub-atmospheric pressure. Compound 13 was fully converted, with a selectivity to the title compound of more than 80%.

The NMR spectrum of the title compound showed the following absorptions in deuterochloroform:

$\delta = 0.90$ ppm, triplet, C$\underline{H}_3$—
$\delta = 1.33$ ppm, multiplet, CH$_3$—(C$\underline{H}_2$)$_3$
$\delta = 1.6$ ppm, multiplet, C$\underline{H}_2$—CH$_2$—CH
$\delta = 2.04$ ppm, multiplet, C$\underline{H}_2$—CH
$\delta = 4.69$ ppm, double doublet, C$\underline{H}$—CCl$_3$

EXAMPLE XXI

Preparation of 1,1,1-tribromo-3-methyl-2-butyl dichlorophosphite (compound 18).

A 10-ml flask was charged with sodium 1,1,1-tribromo-3-methyl-2-butyl carbonate (compound 11, 1.0 mmol) and phosphorus trichloride (1.1 mmol) and stirred at 40° C. for 1.25 hours. Then, the excess of phosphorus trichloride was evaporated at sub-atmospheric pressure. Compound 11 was fully converted, with a selectivity to the title compound of 85%.

The NMR spectrum of the title compound showed the following absorptions in deuterochloroform:

$\delta = 1.20$ ppm, doublet, C$\underline{H}_3$—C—CH$_3$
$\delta = 1.29$ ppm, doublet, CH$_3$—C—C$\underline{H}_3$; J=6 Hz
$\delta = 2.62$ ppm, multiplet, CH$_3$—C$\underline{H}$—CH$_3$
$\delta = 4.67$ ppm, double doublet, OC$\underline{H}$—CBr$_3$ J=2 Hz and J=12 Hz

EXAMPLE XXII

Preparation of sodium 2,2,2-trichloro-1-(2,2-dimethyl-3-methoxycarbonylcyclopropyl) ethyl carbonate (compound 4).

Methyl cis-2-formyl-3,3-dimethylcyclopropanecarboxylate (6.0 mmol. compound 1) was added with stirring to a solution of sodium trichloroacetate (6.6 mmol) in N,N-dimethylformamide (3.2 ml) present in a 25-ml flask. After 15 minutes' stirring the conversion of the starting carboxylate was 97%, with a selectivity to the title carbonate of more than 90%. The carbonate was a mixture of diastereo isomer a (74%) and diastereo isomer b (26%). The NMR spectrum showed the following absorptions in N,N-dimethylformamide:

diastereo isomer a:
$\delta = 1.20$ ppm, singlet, C—C$\underline{H}_3$ and $\delta = 1.43$ ppm, singlet, C—C$\underline{H}_3$
$\delta = 1.80$ ppm, broad singlet, Cl$_3$C—CH—C$\underline{H}$—C$\underline{H}$—C═O
$\delta = 5.47$ ppm, broad singlet, Cl$_3$C—C$\underline{H}$
$\delta = 3.73$ ppm, singlet, —O—C$\underline{H}_3$ diastereo isomer b:
$\delta = 1.20$ ppm, singlet, C—C$\underline{H}_3$ and $\delta = 1.34$ ppm, singlet, C—C$\underline{H}_3$
$\delta = 1.80$ ppm, broad singlet, Cl$_3$C—CH—C$\underline{H}$—C$\underline{H}$—C═O
$\delta = 5.96$ ppm, doublet, Cl$_3$C—C$\underline{H}$; J=9 Hz
$\delta = 3.67$ ppm, singlet, —O—C$\underline{H}_3$

EXAMPLE XXIII

Preparation of methyl 2-(2,2,2-trichloro-1-hydroxyethyl)-3,3-dimethylcyclopropanecarboxylate (compound 27) starting from compound 4

To the reaction mixture obtained in Example XXII 36%w aqueous hydrochloric acid (0.6 ml) was added, which caused evolution of carbon dioxide. Then, water (50 ml) was added and the mixture obtained was extracted with three 15-ml portions of n-pentane. The combined extract phases were washed with water (20 ml) and a saturated aqueous solution of sodium hydrogen carbonate (20 ml). The washed liquid was dried over anhydrous magnesium sulphate and the n-pentane was evaporated at sub-atmospheric pressure from the dried liquid to give a residue (1.47 g) having a content of the title alcohol of 95%, the yield thereof being 85%. The title alcohol is believed to be novel. The carboxylate was a mixture of diastereo isomer c (80%) and diastereo isomer d (20%).

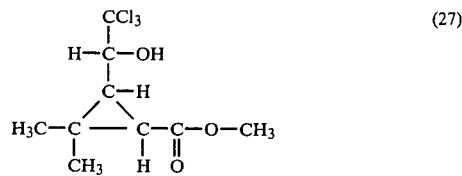

(27)

The NMR spectrum showed the following absorptions in deuterochloroform:

diastereo isomer c:
$\delta = 1.23$ ppm, singlet, CH$_3$—C—C$\underline{H}_3$ and $\delta = 1.35$ ppm, singlet, C$\underline{H}_3$—C—CH$_3$
$\delta = 1.62$ ppm, double doublet, Cl$_3$C—CH—C$\underline{H}$—CH
$\delta = 1.80$ ppm, doublet, HC—C$\underline{H}$—C═O; J=7.5 Hz
$\delta = 3.73$ ppm, singlet, —O—C$\underline{H}_3$
$\delta = 3.95$ ppm, doublet, —O$\underline{H}$; J=6 Hz $\delta = 4.47$ ppm, double doublet, Cl$_3$C—C$\underline{H}$; J=9 Hz diastereo isomer d:
$\delta = 1.29$ ppm, singlet, C—C$\underline{H}_3$ and $\delta = 1.44$ ppm, singlet, C—C$\underline{H}_3$
$\delta = 1.58$ ppm, double doublet, Cl$_3$C—CH—C$\underline{H}$—CH
$\delta = 1.84$ ppm, doublet, HC—C$\underline{H}$—C═O; J=7.5 Hz
$\delta = 3.67$ ppm, singlet, —O—C$\underline{H}_3$
$\delta = 3.02$ ppm, doublet, —O$\underline{H}$; J=6 Hz
$\delta = 4.87$ ppm, double doublet, Cl$_3$C—C$\underline{H}$; J=9 Hz.

EXAMPLE XXIV

Preparation of 2,2-dimethyl-3-(2,2,2-trichloro-1-hydroxyethyl)cyclopropanecarboxylic acid (compound 28)

2-Hydroxy-3-oxa-4-oxo-6,6-dimethylbicyclo[3.1.0-]hexane (0.75 mmol) and sodium trichloroacetate (1.5 mmol) were dissolved in N,N-dimethylformamide (0.5 ml). After 30 min' stirring sodium 2-formyl-3,3-dimethylcyclopropanecarboxylate was formed, with formation of carbon dioxide and chloroform. After 16 hours standing at 20° C. the molar ratio between the sodium 2,2,2-trichloro-1-(2-carboxy-3,3-dimethylcyclopropyl)ethyl carbonate (compound 5) and the starting aldehyde was 23 to 77. After addition of sodium trichloroacetate (0.75 mmol) and 3.75 hours' stirring at 20° C. this ratio was 40 to 60. Stirring was continued for 24 hours. The mixture was acidified with 36%w aqueous hydrochloric acid (0.1 ml), the acidified mixture was extracted with deuterochloroform (0.4 ml), the extract phase was washed with five portions of 1 ml water, the washed liquid was dried over anhydrous magnesium sulphate and the dried liquid was analysed. The conversion of the starting aldehyde was 90%, with a selectivity to the title compound of more than 70%. The title compound is believed to be novel.

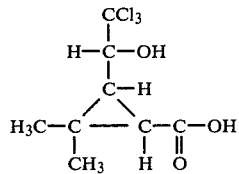

(28)

The NMR spectrum of the title compound showed the following absorptions in deuterochloroform:

δ=1.22 ppm, singlet CH$_3$—C—CH$_3$
δ=1.36 ppm, singlet CH$_3$—C—CH$_3$
δ=1.65 ppm, double doublet CH—CH—CH
δ=1.83 ppm, doublet

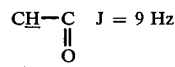
J = 9 Hz

δ=4.47 ppm, doublet Cl$_3$C—OH
δ=5.98 ppm, broad singlet OH and —COOH

EXAMPLE XXV

Preparation of methyl 2-(3,3,3-trichloro-2-hydroxypropyl)-3,3-dimethylcyclopropylmethyl ketone (compound 23)

An NMR tube was charged with sodium trichloroacetate (1.03 mmol), 2,2-dimethyl-3-(2-oxopropyl)cyclopropylethanal (0.70 mmol, compound 3) and N,N-dimethylformamide (0.4 ml). After 16 hours' stirring at 20° C.—the reaction mixture contained sodium 3-[2,2-dimethyl-3-(2-oxopropyl)cyclopropyl]-1,1,1-trichloro-2-propyl carbonate, compound 7, —a 36%w aqueous solution (0.1 ml) of hydrochloric acid was added and the mixture obtained was extracted with deuterochloroform (0.4 ml). The extract phase was washed with three 1-ml portions of water and then analysed. The conversion of the starting aldehyde was more than 95% with a selectivity to the title compound of 70%.

The NMR spectrum of the title compound showed the following absorptions in deuterochloroform:

δ=0.97 ppm, singlet, CH$_3$—C—CH$_3$
δ=1.13 ppm, singlet, CH$_3$—C—CH$_3$
δ=2.21 ppm, singlet, and δ=2.22 ppm, singlet, CH$_3$—C(O)
δ=2.44 ppm, multiplet, C(O)—CH$_2$—
δ=4.02 ppm, triplet, HC—OH

EXAMPLES XXVI-XXVIII

Preparation of three carbonates and three alcohols

An NMR tube was charged with a carbonyl compound (0.50 mmol), sodium trichloroacetate (0.55 mmol) and N,N-dimethylformamide (0.4 ml). After 30 minutes' shaking it was determined which carbonate was present. Then, water (1 ml) was added, the mixture was diluted with deuterochloroform (0.4 ml) and the diluted solution was washed with three portions of 1 ml water. Then it was determined which alcohol was present. Three experiments were thus carried out, each with a different carbonyl compound. Table II states which carbonyl compounds were used and which carbonates and alcohols were formed.

TABLE II

| Ex. | Carbonyl compound | Carbonate formed | compound No. | Alcohol formed |
|---|---|---|---|---|
| XXVI | cyclohexanone | sodium 1-trichloromethylcyclohexyl carbonate | 14 | 1-trichloromethylcyclohexanol |
| XXVII | cyclohexanecarbaldehyde | sodium 2 . 2,2-trichloro-1-cyclohexylethyl carbonate | 8 | 2 . 2,2-trichloro-1-cyclohexylethanol |
| XXVIII | acetone | sodium 1,1,1-trichloro-2-methyl-2-propyl carbonate | 16 | 1,1,1-trichloro-2-methyl-2-propanol |

EXAMPLE XXIX

Preparation of 2,2,2-trichloro-1-(2,2-dimethyl-3-methoxycarbonylcyclopropyl)ethyl dichlorophosphite (compound 21)

A 10-ml flask was charged with sodium 2,2,2-trichloro-1-(2,2-dimethyl-3-methoxycarbonylcyclopropyl)ethyl carbonate (compound 4, 0.73 mmol) and phosphorus trichloride (0.80 mmol) and stirred at 40° C. for 45 min. Then, the excess of phosphorus trichloride was removed at sub-atmospheric pressure. The conversion of compound 4 was at least 92%, with a selectivity to the title compound of at least 79%.

EXAMPLE XXX

Preparation of compound 9 and conversion thereof with acetyl chloride into 1,1,1-trichloro-3-methyl-2-butyl acetate An NMR tube was charged with isobutyraldehyde (0.70 mmol) and N,N-dimethylformamide (0.4 ml) and kept at 80° C. Then, sodium trichloroacetate (0.92 mmol) was added over a period of one minute with shaking. After one minute's shaking the conversion of isobutyraldehyde was 95%, with a selectivity to compound 9 of 75%. After 30 minutes at 20° C. acetyl chloride (0.92 mmol) was added, which caused evolution of carbon dioxide and precipitation of sodium chloride. The yield of the title acetate was 60%; 1,1,1-trichloro-3-methyl-2-butanol was present in a yield of 25%.

EXAMPLE XXXI

Preparation of compound 9 and conversion thereof with acetic anhydride into 1,1,1-trichloro-3-methyl-2-butyl acetate A 100-ml flask was charged with trichloroacetic acid (0.10 mol) and N,N-dimethylformamide (25 ml) was then with potassium fluoride (0.12 mol), which caused the temperature to rise from 20° to 55° C. with vigorous evolution of carbon dioxide. After cooling to 28° C. isobutyraldehyde (0.09 mol) was added, which caused the temperature to rise to 36.5° C. after 15 minutes. At this moment conversion of isobutyraldehyde was 50% and the selectivity to 1,1,1-trichloro-3-methyl-2-butaTol 100%. Then, acetic anhydride (0.12 mol) was added, which caused the temperature to rise from 22° to 41° C. within 35 minutes. As the mixture obtained was difficult to stir it was heated to 80° C. and stirred at this temperature for 30 minutes. The mixture was cooled to 60° C., water (10 ml) was added and the mixture was allowed to adopt a temperature of 20° C. Then, the mixture was taken up in n-pentane (50 ml), the solution obtained was washed with three portions of 30 ml water, the washed solution was dried and the n-pentane was evaporated from the dried solution to give a residue (14.7 g) of the title acetate, the yield thereof being 62.5%.

We claim:

1. A compound of the formula

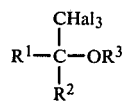

wherein $R^1$ represents a 2-(2,2-dimethoxyethyl)-3,3-dimethylcyclopropyl group, a 2-hydroxycarbonyl-3,3-dimethylcyclopropyl group, a [2,2-dimethyl-3-(2-oxopropyl)cyclopropyl]methyl group or a 2-alkoxycarbonyl-3,3-dimethylcyclopropyl group in which the alkoxy substituent has fewer than five carbon atoms; $R^2$ represents a hydrogen atom; each Hal represents a chlorine or bromine atom; and $R^3$ represents a group $-PX_2$ in which X represents a chlorine or bromine atom.

2. A compound according to claim 1, in which $R^1$ in formula I represents a 2-alkoxycarbonyl-3,3-dimethylcyclopropyl group, in which the alkoxy group has fewer than five carbon atoms.

3. A compound according to claim 2, in which $R^1$ in formula I represents a 2-methoxycarbonyl-3,3-dimethylcyclopropyl group.

4. A compound according to claim 1, in which $R^1$ in formula I represents a 2-(2,2-dimethoxyethyl)-3,3-dimethylcyclopropyl group or a 2-hydroxycarbonyl-3,3-dimethylcyclopropyl group.

5. Compounds as claimed in claim 1, in which $R^1$ represents a [2,2-dimethyl-3-(2-oxopropyl)cyclopropyl]methyl group.

6. 2,2,2-Trichloro-1-(2,2-dimethyl-3-methoxycarbonylcyclopropyl)ethyl dichlorophosphite.

* * * * *